(12) United States Patent
Wong et al.

(10) Patent No.: US 10,344,223 B2
(45) Date of Patent: Jul. 9, 2019

(54) PROCESS FOR PRODUCING BTX

(71) Applicant: SABIC Global Technologies B.V., Bergen op Zoom (NL)

(72) Inventors: Kae Shin Wong, Geleen (NL); Christoph Dittrich, Geleen (NL); Emiel van Kimmenade, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 93 days.

(21) Appl. No.: 15/571,599

(22) PCT Filed: May 3, 2016

(86) PCT No.: PCT/EP2016/059927
§ 371 (c)(1),
(2) Date: Nov. 6, 2017

(87) PCT Pub. No.: WO2016/177749
PCT Pub. Date: Nov. 10, 2016

(65) Prior Publication Data
US 2019/0127646 A1 May 2, 2019

(30) Foreign Application Priority Data

May 6, 2015 (EP) .................................... 15166500

(51) Int. Cl.
*C10G 47/18* (2006.01)
*C07C 4/06* (2006.01)
(Continued)

(52) U.S. Cl.
CPC ............ *C10G 47/18* (2013.01); *B01J 8/0492* (2013.01); *B01J 29/46* (2013.01); *C07C 4/06* (2013.01);
(Continued)

(58) Field of Classification Search
CPC ............ C10G 47/18; C10G 2300/1044; C10G 2400/30; B01J 29/46; B01J 8/0492;
(Continued)

(56) References Cited

U.S. PATENT DOCUMENTS 4,211,634 A 7/1980 Bertolacini et al.
6,299,759 B1 10/2001 Bradway et al.
(Continued)

FOREIGN PATENT DOCUMENTS

WO 2012006316 A1 1/2012
WO 2012015575 A1 2/2012
(Continued)

OTHER PUBLICATIONS

Baerlocher et al.; "Atlas of Zeolite Framework Types"; Elsevier, Fifth Revised Edition, 2001, pp. 1-308.
(Continued)

*Primary Examiner* — In Suk C Bullock
*Assistant Examiner* — Jason Y Chong
(74) *Attorney, Agent, or Firm* — Cantor Colburn LLP

(57) ABSTRACT

The invention relates to a process for hydrocracking a feedstream comprising hydrocarbons to obtain BTX in a gas phase hydrocracking reactor system which comprises (i) an upstream end and a downstream end, (ii) a plurality of successive reaction zones distributed along the reactor between the upstream end and the downstream end, wherein each of the reaction zones has a bed of a hydrocracking catalyst contained therein and (iii) a plurality of quench zones, the quench zones being distributed along the reactor and each being situated between successive reaction zones, wherein the process comprises: (a) injecting a first portion of a hydrogen gas into the upstream end and a first portion of a hydrocarbon gas into the upstream end and (b) injecting a second portion of the hydrogen gas into at least one of the
(Continued)

Figure 1:
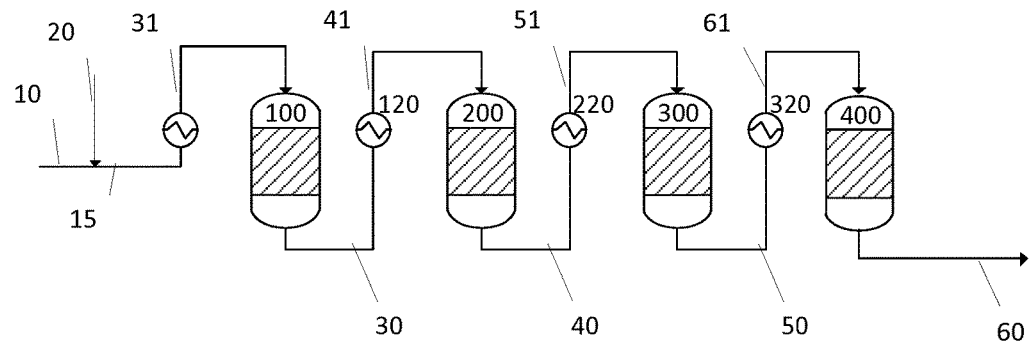

quench zones and injecting a second portion of the hydrocarbon gas into at least one of the quench zones, wherein the molar ratio between hydrogen and hydrocarbons entering each of the reaction zones is 1:1 to 4:1, wherein the molar ratio between hydrogen and hydrocarbons entering the reaction zones decreases with the distance of the reaction zone from the upstream end of the reactor.

14 Claims, 2 Drawing Sheets

(51) Int. Cl.
  *B01J 8/04* (2006.01)
  *B01J 29/46* (2006.01)
(52) U.S. Cl.
  CPC ...... *C07C 2521/12* (2013.01); *C07C 2529/40* (2013.01); *C07C 2529/44* (2013.01); *C10G 2300/1044* (2013.01); *C10G 2400/30* (2013.01)
(58) Field of Classification Search
  CPC ... C07C 4/06; C07C 2521/12; C07C 2529/40; C07C 2529/44
  See application file for complete search history.

(56) References Cited

U.S. PATENT DOCUMENTS

| | | |
|---|---|---|
| 8,221,706 B2 | 7/2012 | Petri et al. |
| 8,324,438 B2 | 12/2012 | Brandvold et al. |
| 8,329,967 B2 | 12/2012 | Brandvold et al. |
| 8,329,968 B2 | 12/2012 | Brandvold et al. |
| 8,518,241 B2 | 8/2013 | Petri et al. |
| 2002/0144930 A1 | 10/2002 | Moore, Jr. |
| 2012/0273394 A1 | 11/2012 | Banerjee et al. |
| 2012/0305446 A1 | 12/2012 | Daily |
| 2015/0060331 A1 | 3/2015 | Sechrist et al. |
| 2015/0073186 A1 | 3/2015 | Banerjee et al. |

FOREIGN PATENT DOCUMENTS

| | | |
|---|---|---|
| WO | 2013135973 A1 | 9/2013 |
| WO | 2013182534 A1 | 12/2013 |

OTHER PUBLICATIONS

Bhirud, "Chances for Innovative Processes at the Interface between Refining and Petrochemistry" Proceedings of the DGMK Conference (2002), pp. 115-122.
Henkel, Klaus-Dieter, "Reactor Types and Their Industrial Chemistry, Applications", Ulmann's Encyclopedia of Industrial 2000, vol. 31, p. 308.
International Search Report for International Application No. PCT/EP2016/059927; dated Jul. 12, 2016; 4 pages.
Kirk-Othmer Encyclopedia of Chemical Technology, "Molecular Sieves," Fifth Edition, vol. 16, (2006), pp. 811-853.
Le Page, "Applied Heterogeneous Catalysis: Design, Manufacture, Use of Solid Catalysts," (1987) Institut Francais due Petrole Publications; pp. 1-4.
Scherzer et al., Hydrocracking Science and Technology, 1996, pp. 13-14 and 174.
Written Opinion of the International Search Report for International Application No. PCT/EP2016/059927; dated Jul. 12, 2016; 7 pages.

PROCESS FOR PRODUCING BTX

CROSS REFERENCE TO RELATED APPLICATIONS

This application is a 371 of International Application No. PCT/EP2016/059927, filed May 3, 2016, which claims priority to European Application No. 15166500.7 filed May 6, 2015, both of which are incorporated herein by reference in their entirety.

The present invention relates to a process for producing BTX from a mixed feedstream in a multiple catalyst bed gas phase reactor.

In exothermic industrial fixed-bed reactors, reactor temperature increases as the reacting stream moves down through the catalyst bed. For this reason, temperature control is a major concern of hydroprocessing operations. Usually, the total heat release is limited to smaller and safer portions by dividing the total catalyst volume into several beds for cooling between the beds.

Henkel, K. D. 2000, Reactor Types and Their Industrial Applications, Ullmann's Encyclopedia of Industrial Chemistry, Vol. 31, p. 308 describes various types of temperature control in fixed-bed catalytic reactors for gas-phase reactions. This document describes cold gas or steam injection (quench gas injection) as well as interstage cooling using heat exchangers for a multibed reactor.

Use of heat exchangers requires a relatively complex reaction system in that extra pipings are necessary. Quench gas injection requires a less complex reaction system, but may lead to a large reactor volume. For gas phase reactors for hydrocracking, the quench fluids are usually hydrogen. The quenching by hydrogen has a problem that it leads to a larger reactor volume especially in when the temperature increase during the reaction is large. Further, the addition of the quench hydrogen gas changes the ratio between hydrogen and hydrocarbons. When the amount of the quench hydrogen gas required for maintaining the acceptable temperature is large, the ratio between hydrogen and hydrocarbons becomes larger than the desired range of the ratio.

It would be desirable to provide a process for converting a hydrocarbon feed stream in a gas phase hydrocracking reactor in which the capital expenditure required is reduced.

It is an object of the present invention to provide a process for hydrocracking hydrocarbons in which above and/or other needs are met.

Accordingly, the present invention provides a process for hydrocracking a feedstream comprising hydrocarbons to obtain BTX in a gas phase hydrocracking reactor system which comprises (i) an upstream end and a downstream end, (ii) a plurality of successive reaction zones distributed along the reactor between the upstream end and the downstream end, wherein each of the reaction zones has a bed of a hydrocracking catalyst contained therein and (iii) a plurality of quench zones, the quench zones being distributed along the reactor and each being situated between successive reaction zones, wherein the process comprises:

(a) injecting a first portion of a hydrogen gas into the upstream end and a first portion of a hydrocarbon gas into the upstream end and (b) injecting a second portion of the hydrogen gas into at least one of the quench zones and injecting a second portion of the hydrocarbon gas into at least one of the quench zones, wherein the molar ratio between hydrogen and hydrocarbons entering each of the reaction zones is 1:1 to 4:1.

Preferably, the present invention provides a process for hydrocracking a feedstream comprising hydrocarbons to obtain BTX in a gas phase hydrocracking reactor system which comprises (i) an upstream end and a downstream end, (ii) a plurality of successive reaction zones distributed along the reactor between the upstream end and the downstream end, wherein each of the reaction zones has a bed of a hydrocracking catalyst contained therein and (iii) a plurality of quench zones, the quench zones being distributed along the reactor and each being situated between successive reaction zones, wherein the process comprises:

(a) injecting a first portion of a hydrogen gas into the upstream end and a first portion of a hydrocarbon gas into the upstream end and (b) injecting a second portion of the hydrogen gas into at least one of the quench zones and injecting a second portion of the hydrocarbon gas into at least one of the quench zones, wherein the molar ratio between hydrogen and hydrocarbons entering each of the reaction zones is 1:1 to 4:1, wherein the molar ratio between hydrogen and hydrocarbons entering the reaction zones decreases with the distance of the reaction zone from the upstream end of the reactor.

It will be appreciated that the first portion of the hydrocarbon gas injected into the upstream end in step (a) and the second portion of the hydrocarbon gas injected into the quench zones in step (b) are portions of the feedstream comprising hydrocarbons to be hydrocracked to obtain BTX. Accordingly, the present invention may also be described as a process for hydrocracking a feedstream comprising hydrocarbons to obtain BTX in a gas phase hydrocracking reactor system which comprises (i) an upstream end and a downstream end, (ii) a plurality of successive reaction zones distributed along the reactor between the upstream end and the downstream end, wherein each of the reaction zones has a bed of a hydrocracking catalyst contained therein and (iii) a plurality of quench zones, the quench zones being distributed along the reactor and each being situated between successive reaction zones, wherein the process comprises:

(a) injecting a first portion of a hydrogen gas into the upstream end and a first portion of a hydrocarbon gas which is the feedstream comprising hydrocarbons into the upstream end and (b) injecting a second portion of the hydrogen gas into at least one of the quench zones and injecting a second portion of the hydrocarbon gas into at least one of the quench zones, wherein the molar ratio between hydrogen and hydrocarbons entering each of the reaction zones is 1:1 to 4:1, wherein the molar ratio between hydrogen and hydrocarbons entering the reaction zones decreases with the distance of the reaction zone from the upstream end of the reactor.

The process according to the invention is a process for hydrocracking hydrocarbons in a gas phase reactor system having multiple reaction zones. Each of the reaction zones is followed by a quench zone, except the reaction zone closest to the downstream end (hereinafter sometimes referred as the last reaction zone).

The gas phase reactor system in the process according to the invention may comprise a plurality of gas phase reactors each comprising a reaction zone. Alternatively, the gas phase reactor system in the process according to the invention may comprise a single gas phase reactor comprising a plurality of reaction zones.

The quench zone is herein understood as an apparatus between successive reactors or as a zone between successive reaction zones in a reactor, in which an effluent from the previous reaction zone and a quench gas are mixed. The quench zone does not include a heat exchanger using a coolant to cool the stream which passes through the heat exchanger.

In the reaction zones, the hydrocarbons contact the hydrocracking catalyst in the presence of hydrogen to be hydrocracked. The reaction generates heat and the ratio of hydrogen to hydrocarbons decreases, and the effluent from the reaction zone enters the quench zone. The second portion of the hydrogen gas and the second portion of the hydrocarbon gas have lower temperatures than the effluent to which they are added. In the quench zone, the effluent is mixed with the cooler hydrogen gas and/or cooler hydrocarbons gas to remove the heat of the effluent. The addition of the cooler hydrogen gas and/or cooler hydrocarbons gas in each of the quench zones is performed such that the molar ratio between hydrogen and hydrocarbons in the resulting mixture is within the desired range of 1:1 to 4:1.

The ratio of the hydrogen gas and the hydrocarbon gas entering the reaction zones influences the reactor size, the purity of benzene obtained and coke formation. An excess amount of hydrogen in the reaction mixture suppresses the coke formation which is believed to lead to catalyst deactivation. On the other hand, a higher hydrogen content will lead to a larger reactor volume. It has also previously been reported that a higher benzene purity (amount of benzene with respect to the total amount of C6 hydrocarbons) in the product stream can be obtained by selecting a relatively low molar ratio between hydrogen and hydrocarbons. Therefore, the ratio between the hydrogen and the hydrocarbons must be within a certain range for suppression of the coke formation while allowing a reasonable reactor size and a high benzene purity. The ratio between the hydrogen and the hydrocarbons of 1:1 to 4:1 leads to sufficient suppression of the coke formation while allowing a reasonable reactor size and a high benzene purity.

Accordingly, the second portion of the hydrogen gas and the second portion of the hydrocarbons gas which act as quench gas are also advantageously used to control the reaction and required reactor size. Unlike systems in which only hydrogen or only hydrocarbon is used as a quench gas, the use of both hydrogen and hydrocarbon as a quench gas allows precise control of the ratio between the hydrogen and the hydrocarbons in each of the reaction zones.

Heat exchangers are not used between reaction zones in the process of the invention. This allows operating in a single reactor comprising a plurality of reactor zones separated by quench zones. Accordingly, in some embodiments of the process of the invention, the gas phase hydrocracking reactor system comprises a single reactor comprising the reaction zones and the quench zones. A single reactor is advantageous in view of economic considerations (CAPEX), for example requiring smaller building areas. Further, due to the absence of heat exchangers and related pipings, lower pressure drop is achieved across the reactor system. The low pressure drop across the reactor system is desirable for the easier control of the pressure in each of the reaction zones.

The reaction zones closer to the upstream of the reactor are more prone to catalyst deactivation than the reaction zones closer to the downstream end since the amount of components which cause catalyst deactivation is larger in the reaction zones closer to the upstream end of the reactor. Accordingly, the molar ratio between hydrogen and hydrocarbon is preferably relatively high in the reaction zones close to the upstream end. The molar ratio between hydrogen and hydrocarbon is preferably relatively low in the reaction zones close to the downstream end which are less prone to catalyst deactivation, for increasing the BTX purity and reducing the reactor size.

Accordingly, preferably, the molar ratio between hydrogen and hydrocarbons entering the reaction zones decreases with the distance from the upstream end of the reactor.

It is noted that US2015/073186 discloses a method for hydrotreating a naphtha blend stream, comprising providing a hydrotreater reactor having a first input disposed at a first bed and a second input disposed at a second bed bypassing the first bed; admitting the naphtha blend stream to the reactor via a charge heater, wherein the stream is split so that the stream is admitted to the reactor at both the first input and the second input; measuring a temperature difference across the first bed; controlling distribution of the naphtha blend at the second input based on the measured temperature difference.

US2015/073186 does not disclose the molar ratio between hydrogen and hydrocarbons entering each of the reaction zones of 1:1 to 4:1. US2015/073186 further does not disclose that the molar ratio between hydrogen and hydrocarbons entering the reaction zones decreases with the distance of the reaction zone from the upstream end of the reactor.

Preferably, the molar ratio between hydrogen and hydrocarbons entering the reaction zone closest to the downstream end (hereinafter sometimes referred as the last reaction zone) is at least 25% (for example 25%-50%) lower than the molar ratio between hydrogen and hydrocarbons entering the reaction zone closest to the upstream end (hereinafter sometimes referred as the first reaction zone). For example, when the molar ratio between hydrogen and hydrocarbons entering the first reaction zone is 3:1, the molar ratio between hydrogen and hydrocarbons entering the last reaction zone is at most 2.25:1 (25% lower).

Preferably, the molar ratio between hydrogen and hydrocarbons entering the reaction zone closest to the upstream end is 1.5:1 to 4:1, more preferably 2:1 to 4:1, more preferably 3:1 to 4:1.

Preferably, the molar ratio between hydrogen and hydrocarbons entering the reaction zone closest to the downstream end is 1:1 to 3:1, more preferably 1:1 to 2.5:1, more preferably 1:1 to 2:1, more preferably 1:1 to 1.5:1.

The amounts of the second portion of the hydrogen gas and the second portion of the hydrocarbons gas are determined according to the desired temperature to be achieved. Preferably, the amounts of the second portion of the hydrogen gas and the second portion of the hydrocarbons gas are chosen such that the temperatures of the streams entering subsequent reaction zones are not more than 80° C. higher than the stream entering the first reaction zone.

The number of reaction zones and the allowed temperature increase are to be decided based on the desired composition of the hydrocracking product stream and economic considerations (CAPEX).

Preferably, the hydrocracking product stream has a relatively low molar ratio between hydrogen and hydrocarbon, e.g. at most 2:1, at most 1.5:1, at most 1:1. The hydrocracking product stream typically has a molar ratio between hydrogen and hydrocarbon of at least 1:1, but it is also possible that said molar ratio is below 1:1, for example 0.1:1 to 0.75:1, 0.1:1 to 0.5:1 or 0.1:1 to 0.25:1. The lower molar ratio is advantageous for a smaller size of the reactor.

It is noted that U.S. Pat. No. 6,299,759 discloses a method for catalytic hydrotreating and hydrocracking liquid hydrocarbon feedstocks. In this method, a liquid hydrocarbon feed and a quench gas (hydrogen) are injected into quench zones between reaction zones. In the hydrotreating and hydrocracking method using liquid hydrocarbon feedstocks, the amount of hydrogen which reacts with hydrocarbons is largely controlled by the conditions of the reaction zone, e.g. pressure, rather than the feed ratio between hydrogen gas and liquid hydrocarbons. Therefore, U.S. Pat. No. 6,299,759 does not teach controlling the ratio between the hydrogen feed and the hydrocarbon feed in each of the reaction zones using a hydrocarbon feed and a quench gas.

In the process according to the invention, the second portion of the hydrogen gas and the second portion of the hydrocarbon gas to be injected into the quench zones may be distributed among various quench zones in any manner. The amount of the gas injected into each of the quench zones may be the same or different. For example, the second portion of the hydrogen gas may be evenly split to be fed to each of the quench zones and the second portion of the hydrocarbon gas may be split such that the amount of the hydrocarbon gas to be injected into the quench zone closer to the upstream end may be higher than the amount of the hydrocarbon gas to be injected into the quench zone closer to the downstream end.

In each of the quench zones, the hydrocarbon gas and the hydrogen gas may be injected as separate streams or as a mixture. Preferably, at least one of the hydrocarbon gas, the hydrogen gas and the mixture is injected into each of the quench zones. It is however possible that none of the hydrocarbon gas, the hydrogen gas and the mixture is injected in some of the quench zones.

In some embodiments, either the hydrocarbon gas or the hydrogen gas is injected to each of the quench zones. In this case, preferably, the hydrocarbon gas and the hydrogen gas are injected into the quench zones alternately.

In some embodiments, a mixture of the hydrocarbon gas and the hydrogen gas is injected into each of the quench zones. The ratio between hydrogen and hydrocarbon may be selected at any ratio to achieve the desired ratio between hydrogen and hydrocarbon in the mixture entering the reaction zones.

In this context the term "hydrocarbons entering the reaction zone" or "hydrocarbons in the reaction zone" means all hydrocarbon molecules present in the hydrocarbon gas such as benzene, toluene, hexane, cyclohexane etc. It is necessary to know the composition of the hydrocarbon gas to then calculate the average molecular weight of this stream to be able to calculate the molar ratio between hydrogen and hydrocarbons.

Preferably, the process according to the invention produces a hydrocracking product stream comprising BTX and LPG. Preferably, the hydrocracking product stream is substantially free from non-aromatic C6+ hydrocarbons.

The number of the reaction zones in the reaction system may be any number, typically 2-10, more typically 3-8 or 3-5.

As used herein, the term "C# hydrocarbons", wherein "#" is a positive integer, is meant to describe all hydrocarbons having # carbon atoms. Moreover, the term "C#+ hydrocarbons" is meant to describe all hydrocarbon molecules having # or more carbon atoms. Accordingly, the term "C5+ hydrocarbons" is meant to describe a mixture of hydrocarbons having 5 or more carbon atoms.

The term "LPG" as used herein refers to the well-established acronym for the term "liquefied petroleum gas". LPG generally consists of a blend of C2-C4 hydrocarbons i.e. a mixture of C2, C3, and C4 hydrocarbons.

The term "BTX" as used herein is well known in the art and relates to a mixture of benzene, toluene and xylenes.

The term "aromatic hydrocarbon" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

Feed Stream

Preferably, the feed stream used in the process of the present invention is a mixture comprising C5-C12 hydrocarbons. Preferably, the source feed stream comprises at least 40 wt %, more preferably at least 45 wt %, most preferably at least 50 wt % of the C5-C12 hydrocarbons. Preferably, the feed stream mainly comprises C6-C8 hydrocarbons. Preferably the feed stream has a boiling point in the range of 30-195° C. Suitable hydrocracking feed streams include, but are not limited to first stage or multi-stage hydro-treated pyrolysis gasoline, straight run naphtha, hydrocracked gasoline, light coker naphtha and coke oven light oil, FCC gasoline, reformate, FT (Fischer-Tropsch) or synthetic naphtha, or mixtures thereof. The feed stream may have a relatively high sulphur content, such as pyrolysis gasoline (pygas), straight run naphtha, light coker naphtha and coke oven light oil and mixtures thereof. Furthermore, it is preferred that the non-aromatic species comprised in the hydrocarbon feed are saturated (e.g. by prior hydrogenation) in order to reduce the exotherm within the catalyst bed used in the present process.

For instance, a typical composition of pyrolysis gasoline may comprise 10-15 wt-% C5 olefins, 2-4 wt-% C5 paraffins and cycloparaffins, 3-6 wt-% C6 olefins, 1-3 wt-% C6 paraffins and naphthenes, 25-30 wt-% benzene, 15-20 wt-% toluene, 2-5 wt-% ethylbenzene, 3-6 wt-% xylenes, 1-3 wt-% trimethylbenzenes, 4-8 wt-% dicyclopentadiene, and 10-15 wt-% C9+ aromatics, alkylstyrenes and indenes; see e.g. Table E3.1 from Applied Heterogeneous Catalysis: Design, Manufacture, and Use of Solid Catalysts (1987) J. F. Le Page. However, also hydrocarbon mixtures that are depentanised and tailed so the concentrations of all the C6 to C9 hydrocarbon species are relatively high compared with the typical figures above can be advantageously used as a feed stream in the process of the present invention.

In some embodiments, the feed stream used in the process of the present invention is treated so that it is enriched in mono-aromatic compounds. As used herein, the term "mono-aromatic compound" relates to a hydrocarbon compound having only one aromatic ring. Means and methods suitable to enrich the content of mono-aromatic compounds in a mixed hydrocarbon stream are well known in the art such as the Maxene process; see Bhirud (2002) Proceedings of the DGMK-conference 115-122.

The feed stream used in the process of the present invention may comprise up to 300 wppm of sulphur (i.e. the weight of sulphur atoms, present in any compound, in relation to the total weight of the feed).

In preferred embodiments the feed stream is depentanized, which means that the feed stream is substantially free from C5 hydrocarbons. As meant herein, the term "feed stream substantially free from C5 hydrocarbons" means that said feed stream comprises less than 1 wt-% C5 hydrocarbons, preferably less than 0.7 wt-% C5 hydrocarbons, more preferably less than 0.6 wt-% C5 hydrocarbons and most preferably less than 0.5 wt-% C5 hydrocarbons.

The feed stream can be subjected to hydrodesulphurisation before hydrocracking.

Hydrocracking Catalyst

The feed stream is contacted in the presence of hydrogen with a hydrocracking catalyst in each of the catalyst beds in the gas phase reactor.

In preferred embodiments, the hydrocracking catalyst further has a hydrodesulphurisation activity. This is advantageous in that it is not necessary to subject the hydrocarbon feed stream to a desulphurisation treatment prior to subjecting said hydrocarbon feed stream to the hydrocracking treatment.

Catalysts having hydrocracking/hydrodesulphurisation activity ("hydrocracking/hydrodesulphurisation catalyst") are described on pages 13-14 and 174 of Hydrocracking Science and Technology (1996) Ed. Julius Scherzer, A. J. Gruia, Pub. Taylor and Francis. Hydrocracking and hydrodesulphurisation reactions proceed through a bifunctional mechanism which requires a relatively strong acid function, which provides for the cracking and isomerization and which provides breaking of the sulphur-carbon bonds comprised in the organic sulfur compounds comprised in the feed, and a metal function, which provides for the olefin hydrogenation and the formation of hydrogen sulfide. Many catalysts used for the hydrocracking/hydrodesulphurisation process are formed by composting various transition metals with the solid support such as alumina, silica, alumina-silica, magnesia and zeolites.

In preferred embodiments of the invention, the catalyst is a hydrocracking catalyst comprising 0.01-1 wt-% hydrogenation metal in relation to the total catalyst weight and a zeolite having a pore size of 5-8 Å and a silica ($SiO_2$) to alumina ($Al_2O_3$) molar ratio of 5-200 and the process conditions comprise a temperature of 425-580° C., a pressure of 300-5000 kPa gauge and a Weight Hourly Space Velocity of 0.1-15 $h^{-1}$.

In these embodiments, the obtained hydrocracking product stream is advantageously substantially free from non-aromatic C6+ hydrocarbons due to the catalyst and the conditions employed. Hence, chemical grade BTX can easily be separated from the hydrocracking product stream product stream.

The advantageous effects of these embodiments are obtained by strategically selecting the hydrocracking catalyst in combination with the hydrocracking conditions. Hydrocracking is performed under process conditions including a temperature of 425-580° C., a pressure of 300-5000 kPa gauge and a Weight Hourly Space Velocity of 0.1-15 $h^{-1}$. By combining a hydrocracking catalyst having a relatively strong acid function (e.g. by selecting a catalyst comprising a zeolite having a pore size of 5-8 Å and a silica ($SiO_2$) to alumina ($Al_2O_3$) molar ratio of 5-200) and a relatively strong hydrogenation activity (e.g. by selecting a catalyst comprising 0.01-1 wt-% hydrogenation metal) with process conditions comprising a relatively high process temperature (e.g. by selecting a temperature of 425-580° C.), chemical grade BTX and LPG can be produced from the hydrocracking product stream.

Preferably, the hydrocracking of the feed stream is performed at a pressure of 300-5000 kPa gauge, more preferably at a pressure of 600-3000 kPa gauge, particularly preferably at a pressure of 1000-2000 kPa gauge and most preferably at a pressure of 1200-1600 kPa gauge. By increasing reactor pressure, conversion of C5+ non-aromatics can be increased, but also increases the yield of methane and the hydrogenation of aromatic rings to cyclohexane species which can be cracked to LPG species. This results in a reduction in aromatic yield as the pressure is increased and, as some cyclohexane and its isomer methylcyclopentane, are not fully hydrocracked, there is an optimum in the purity of the resultant benzene at a pressure of 1200-1600 kPa.

Preferably, the hydrocracking/hydrodesulphurisation of the feed stream is performed at a Weight Hourly Space Velocity (WHSV) of 0.1-15 $h^{-1}$, more preferably at a Weight Hourly Space Velocity of 1-10 $h^{-1}$ and most preferably at a Weight Hourly Space Velocity of 2-9 $h^{-1}$. When the space velocity is too high, not all BTX co-boiling paraffin components are hydrocracked, so it will not be possible to achieve BTX specification by simple distillation of the reactor product. At too low space velocity the yield of methane rises at the expense of propane and butane. By selecting the optimal Weight Hourly Space Velocity, it was surprisingly found that sufficiently complete reaction of the benzene co-boilers is achieved to produce on spec BTX without the need for a liquid recycle.

Accordingly, preferred hydrocracking conditions thus include a temperature of 425-580° C., a pressure of 300-5000 kPa gauge and a Weight Hourly Space Velocity of 0.1-15 $h^{-1}$. More preferred hydrocracking conditions include a temperature of 450-550° C., a pressure of 600-3000 kPa gauge and a Weight Hourly Space Velocity of 1-10 $h^{-1}$. Particularly preferred hydrocracking conditions include a temperature of 450-550° C., a pressure of 1000-2000 kPa gauge and a Weight Hourly Space Velocity of 2-9 $h^{-1}$.

Hydrocracking catalysts that are particularly suitable for the process of the present invention comprise a molecular sieve, preferably a zeolite, having a pore size of 5-8 Å.

Zeolites are well-known molecular sieves having a well-defined pore size. As used herein, the term "zeolite" or "aluminosilicate zeolite" relates to an aluminosilicate molecular sieve. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001). Preferably, the hydrocracking catalyst comprises a medium pore size aluminosilicate zeolite or a large pore size aluminosilicate zeolite. Suitable zeolites include, but are not limited to, ZSM-5, MCM-22, ZSM-11, beta zeolite, EU-1 zeolite, zeolite Y, faujastite, ferrierite and mordenite. The term "medium pore zeolite" is commonly used in the field of zeolite catalysts. Accordingly, a medium pore size zeolite is a zeolite having a pore size of about 5-6 Å. Suitable medium pore size zeolites are 10-ring zeolites, i.e. the pore is formed by a ring consisting of 10 $SiO_4$ tetrahedra. Suitable large pore size zeolites have a pore size of about 6-8 Å and are of the 12-ring structure type. Zeolites of the 8-ring structure type are called small pore size zeolites. In the above cited Atlas of Zeolite Framework Types various zeolites are listed based on ring structure. Most preferably the zeolite is ZSM-5 zeolite, which is a well-known zeolite having MFI structure.

Preferably, the silica to alumina ratio of the ZSM-5 zeolite is in the range of 20-200, more preferably in the range of 30-100.

The zeolite is in the hydrogen form: i.e. having at least a portion of the original cations associated therewith replaced by hydrogen. Methods to convert an aluminosilicate zeolite to the hydrogen form are well known in the art. A first method involves direct ion exchange employing an acid and/or salt A second method involves base-exchange using ammonium salts followed by calcination.

Furthermore, the catalyst composition comprises a sufficient amount of hydrogenation metal to ensure that the catalyst has a relatively strong hydrogenation activity. Hydrogenation metals are well known in the art of petrochemical catalysts.

The catalyst composition preferably comprises 0.01-1 wt-% hydrogenation metal, more preferably 0.01-0.7 wt-%, most preferably 0.01-0.5 wt-% hydrogenation metal, more preferably 0.01-0.3 wt-%. The catalyst composition may more preferably comprise 0.01-0.1 wt-% or 0.02-0.09 wt-% hydrogenation metal. In the context of the present invention, the term "wt %" when relating to the metal content as comprised in a catalyst composition relates to the wt % (or "wt-%") of said metal in relation to the weight of the total catalyst, including catalyst binders, fillers, diluents and the like. Preferably, the hydrogenation metal is at least one element selected from Group 10 of the Periodic Table of Elements. The preferred Group 10 element is platinum (Pt). Accordingly, the hydrocracking catalyst used in the process of the present invention comprises a zeolite having a pore size of 5-8 Å, a silica ($SiO_2$) to alumina ($Al_2O_3$) molar ratio of 5-200 and 0.01-1 wt-% platinum (in relation to the total catalyst).

The hydrocracking catalyst composition may further comprise a binder. Alumina ($Al_2O_3$) is a preferred binder. The catalyst composition of the present invention preferably comprises at least 10 wt-%, most preferably at least 20 wt-% binder and preferably comprises up to 40 wt-% binder. In some embodiments, the hydrogenation metal is deposited on the binder, which preferably is $Al_2O_3$.

According to some embodiments of the invention, the hydrocracking catalyst is a mixture of the hydrogenation metal on a support of an amorphous alumina and the zeolite. According to other embodiments of the invention, the hydrocracking catalyst comprises the hydrogenation metal on a support of the zeolite. In this case, the hydrogenation metal and the zeolite giving cracking functions are in closer proximity to one another which translates into a shorter diffusion length between the two sites. This allows high space velocity, which translates into smaller reactor volumes and thus lower CAPEX. Accordingly, in some preferred embodiments, the hydrocracking catalyst is the hydrogenation metal on a support of the zeolite and step (b) is performed at a Weight Hourly Space Velocity of 10-15 $h^{-1}$.

In these embodiments where the catalyst is a hydrocracking catalyst comprising 0.01-1 wt-% hydrogenation metal in relation to the total catalyst weight and a zeolite having a pore size of 5-8 Å and a silica ($SiO_2$) to alumina ($Al_2O_3$) molar ratio of 5-200 and the first process conditions comprise a temperature of 425-580° C., a pressure of 300-5000 kPa gauge and a Weight Hourly Space Velocity of 0.1-15 $h^{-1}$, the product produced by the hydrocracking step of the process of the present invention (hydrocracking product stream) mainly comprises hydrogen, methane, LPG and BTX.

According to these embodiments of the present invention, chemical grade BTX can easily be separated from the hydrocracking product stream.

As used herein, the term "chemical grade BTX" relates to a hydrocarbon mixture comprising less than 5 wt-% hydrocarbons other than benzene, toluene and xylenes, preferably less than 4 wt-% hydrocarbons other than benzene, toluene and xylenes, more preferably less than 3 wt-% hydrocarbons other than benzene, toluene and xylenes, and most preferably less than 2.5 wt-% hydrocarbons other than benzene, toluene and xylenes.

Furthermore, the "chemical grade BTX" produced by the process of the present invention comprises less than 1 wt-% non-aromatic C6+ hydrocarbons, preferably less than 0.7 wt-% non-aromatic C6+ hydrocarbons, more preferably less than 0.6 wt-% non-aromatic C6+ hydrocarbons and most preferably less than 0.5 wt-% non-aromatic C6+ hydrocarbons. The most critical contaminants are the non-aromatic species which have boiling points close to benzene including, but not limited to, cyclohexane, methylcyclopentane, n-hexane, 2-methylpentane and 3-methylpentane.

It is a particular advantage of these embodiments that the hydrocracking product stream is substantially free from non-aromatic C6+ hydrocarbons as these hydrocarbons usually have boiling points close to the boiling point of C6+ aromatic hydrocarbons. Hence, it can be difficult to separate the non-aromatic C6+ hydrocarbons from the aromatic C6+ hydrocarbons comprised in the hydrocracking product stream by distillation.

As meant herein, the term "product stream substantially free from non-aromatic C6+ hydrocarbons" means that said product stream comprises less than 1 wt-% non-aromatic C6+ hydrocarbons, preferably less than 0.7 wt-% non-aromatic C6+ hydrocarbons, more preferably less than 0.6 wt-% non-aromatic C6+ hydrocarbons and most preferably less than 0.5 wt-% non-aromatic C6+ hydrocarbons.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

Figure 2:
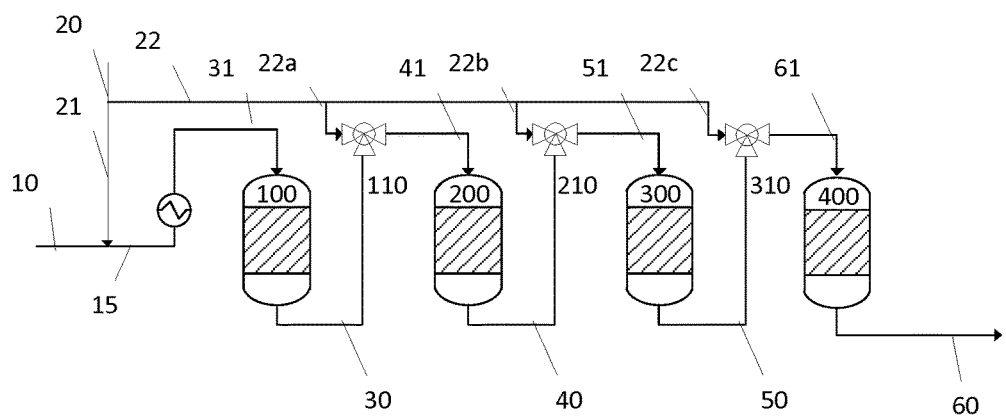
Figure 3:
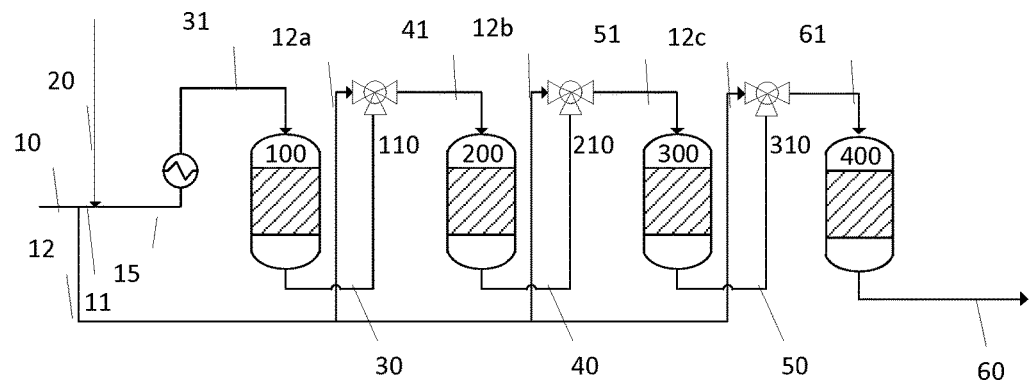
Figure 4:
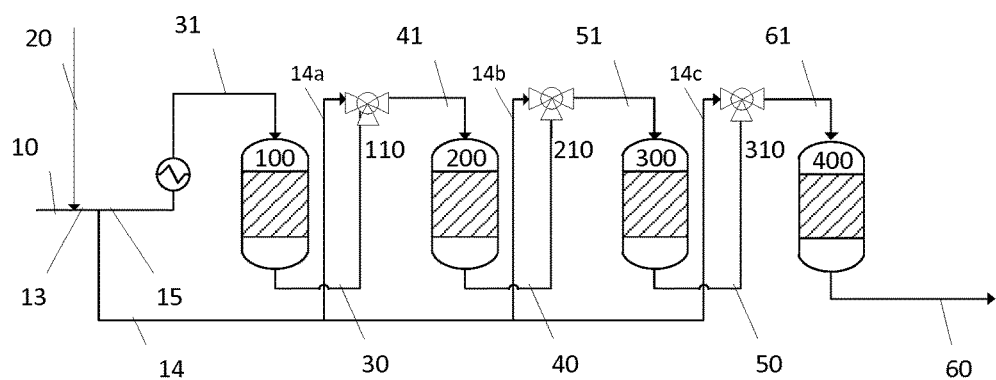
Figure 5:
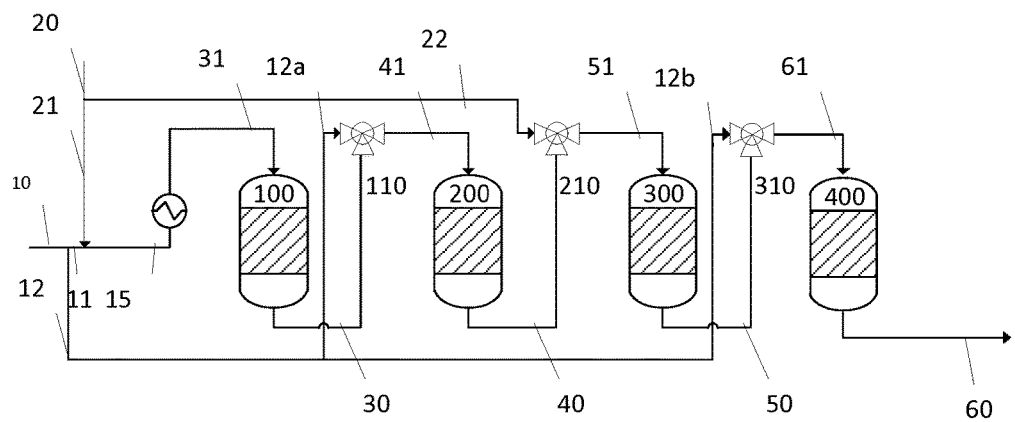

The present invention will now be elucidated by the following non-limiting drawings in which:

FIG. 1 shows a scheme illustrating an example of a gas phase hydrocracking reactor system where cooling of the effluents are performed by heat exchangers, FIGS. 2-3 show schemes illustrating examples of a gas phase hydrocracking reactor system where cooling of the effluents are performed by either a hydrogen gas stream or a hydrocarbon gas stream and FIGS. 4-5 show schemes illustrating examples of a gas phase hydrocracking reactor system where cooling of the effluents are performed by gas streams, which are according to the invention.

Same components of the system are represented by the same reference numbers throughout the figures wherever possible.

FIG. 1 shows a scheme illustrating an example of a conventional gas phase hydrocracking reactor system. The reactor system comprises, from an upstream end to an downstream end, a first catalyst bed 100, a second catalyst bed 200, a third catalyst bed 300 and a fourth catalyst bed 400. Between the first catalyst bed 100 and the second catalyst bed 200, a first heat exchanger 120 is provided. Similarly, a second heat exchanger 220 and a third heat exchanger 320 are provided between successive catalyst beds. Each catalyst bed represents a reaction zone.

Hydrocarbon gas 10 and hydrogen gas 20 to be fed to the first catalyst bed are at room temperature. The mixture 15 of the hydrocarbon gas 10 and hydrogen gas 20 are fed to a heating means to obtain a heated mixture 31 of hydrocarbon and hydrogen. The ratio between hydrogen and hydrocarbon in the heated mixture 31 is in the range of 1:1 to 4:1. The heated mixture 31 is fed to the first catalyst bed 100 set to a desired temperature. The first effluent 30 from the first catalyst bed 100 enters the first heat exchanger 120 which produces a cooled stream 41. The cooled stream 41 enters the second catalyst bed 200. This is repeated until the hydrocracking product stream 60 is obtained from the fourth catalyst bed 400.

FIGS. 2-5 show schemes illustrating examples of a gas phase hydrocracking reactor system where cooling of the effluents are performed by gas streams instead of heat exchangers. FIGS. 4-5 illustrate examples of a gas phase hydrocracking reactor system according to the invention.

FIG. 5 shows a scheme illustrating an example of the gas phase hydrocracking reactor system according to the invention. The reactor system comprises, from an upstream end to an downstream end, a first catalyst bed 100, a second catalyst bed 200, a third catalyst bed 300 and a fourth catalyst bed 400. Between the first catalyst bed 100 and the second catalyst bed 200, a first quench zone 110 is provided. Similarly, a second quench zone 210 and a third quench zone 310 are provided between successive catalyst beds.

Hydrocarbon gas 10 and hydrogen gas 20 to be fed to the reactor are at room temperature. The hydrocarbon gas 10 is first split into a first portion 11 of the hydrocarbon gas which is to be fed to the upstream end of the reactor and a second portion 12 of the hydrocarbon gas which is to be fed to the quench zones. Similarly, the hydrogen gas 20 is split into a first portion 21 of the hydrogen gas which is to be fed to the upstream end of the reactor and a second portion 22 of the hydrogen gas which is to be fed to the quench zones.

The first portion 11 of the hydrocarbon gas and the first portion 21 of the hydrogen gas are mixed to form a mixture 15. The mixture 15 is fed to a heating means to obtain a heated mixture 31 of hydrocarbon and hydrogen. The ratio between hydrogen and hydrocarbon in the heated mixture is in the range of 1:1 to 4:1. The heated mixture 31 is fed to the first catalyst bed 100 set to a desired temperature. The first effluent 30 from the first catalyst bed 100 enters the first quench zone 110.

The second portion 12 of the hydrocarbon gas is further split up into two fractions. One fraction 12a is added to the first quench zone 110 to be mixed with the first effluent 30 from the first catalyst bed 100 to obtain a first quenched mixture 41. By the addition of the hydrocarbon gas 12a having a room temperature, the temperature is lowered and the ratio between hydrogen and hydrocarbon is lowered. The first quenched mixture 41 is fed to the second catalyst bed 200 set to a desired temperature. The second effluent 40 from the second catalyst bed 200 enters the second quench zone 210.

The second portion 22 of the hydrogen gas is added to the second quench zone 210 to be mixed with the second effluent 40 from the second catalyst bed 200 to obtain a second quenched mixture 51. By the addition of the hydrogen gas 22 having a room temperature, the temperature is lowered and the ratio between hydrogen and hydrocarbon is increased. The second quenched mixture 51 is fed to the third catalyst bed 300 set to a desired temperature. The third effluent 50 from the third catalyst bed 300 enters the third quench zone 310. The fraction 12b of the second portion 12 of the hydrocarbon gas is added to the third quench zone 310 to be mixed with the second effluent 50 from the second catalyst bed 300 to obtain a third quenched mixture 61. By the addition of the hydrocarbon gas 12b having a room temperature, the temperature is lowered and the ratio between hydrogen and hydrocarbon is lowered. The quenched mixture 61 is fed to the fourth catalyst bed 400 set to a desired temperature. A hydrocracking product stream 60 is obtained and exits the reactor system from the downstream end.

The addition of the quench gas is performed such that the molar ratio of hydrogen and hydrocarbons in the quenched mixtures entering the catalyst beds is in the range of 1:1 to 4:1.

FIG. 4 shows a scheme illustrating an example of the gas phase hydrocracking reactor system according to the invention. The catalyst beds 100-400 and the quench zones 110-310 in FIG. 4 are the same as the reactor in FIG. 5, but the hydrocarbon gas and hydrogen gas to be fed to the reactor system is first mixed before being split into a first portion 15 which is to be fed to the upstream end of the reactor and a second portion 14 of which is to be fed to the quench zones.

The first portion of the hydrocarbon gas and the first portion of the hydrogen gas are fed as a mixture 15 to a heating means to obtain a heated mixture 31 of hydrocarbon and hydrogen. The ratio between hydrogen and hydrocarbon in the heated mixture 31 is in the range of 1:1 to 4:1. The heated mixture 31 is fed to the first catalyst bed 100 set to a desired temperature. The first effluent 30 from the first catalyst bed 100 enters the first quench zone.

The second portion 14 of the mixture is further split up into three fractions 14a, 14b, 14c. Each of the fractions 14a, 14b, 14c is added to the first quench zone 110, the second quench zone 210 and the third quench zone 310, respectively, to be mixed with the effluent from the previous catalyst bed to decrease the temperature. The third quenched mixture 61 from the third quench zone 310 is fed to the fourth catalyst bed 400 set to a desired temperature. A hydrocracking product stream 60 is obtained and exits the reactor system from the downstream end.

The addition of the quench gas (mixture of hydrocarbon gas and hydrogen gas) is performed such that the molar ratio of hydrogen and hydrocarbons in the quenched mixtures entering the catalyst beds is in the range of 1:1 to 4:1.

FIG. 2 shows a scheme illustrating an example of the gas phase hydrocracking reactor in which only hydrogen gas is used as a quench gas fed to the quench zones. Hydrogen gas 22a, 22b, 22c are fed to the quench zones 110, 210 and 310, respectively.

FIG. 3 shows a scheme illustrating an example of the gas phase hydrocracking reactor in which only hydrocarbon gas is used as a quench gas fed to the quench zones. Hydrocarbon gas 12a, 12b, 12c are fed to the quench zones 110, 210 and 310, respectively.

EXAMPLES

Simulations were carried out using a naphtha feed, the feed composition is shown in Table 1. The reactor is operated at 450° C., 200 psig, weight hourly space velocity of 2.6 $h^{-1}$ and H:HC of 3.

TABLE 1

Naphtha feed composition

| Components | Mass fraction (by wt) |
|---|---|
| Pentane | 0.128 |
| Hexane | 0.130 |
| Methylcyclopentane | 0.083 |
| Benzene | 0.007 |
| Heptane | 0.127 |
| Methylcyclohexane | 0.066 |
| Toluene | 0.014 |
| Octane | 0.090 |
| Ethylcyclehexane | 0.073 |
| Ethylbenzene | 0.027 |
| Nonane | 0.143 |
| Isopropylbenzene | 0.041 |
| Butylbenzene | 0 |
| Decane | 0.071 |
| Total | 1 |

Example 1 (Comparative): Series of Reactors with Interstage Cooling

The hydrocarbon feed is subjected to hydrocracking by a system as illustrated in FIG. 1. The hydrocarbon feed is pre-mixed with hydrogen and heated to reaction temperature before entering the first reactor. Interstage heat exchangers are used to control the reactor temperature. The temperature and the molar ratio of hydrogen to hydrocarbon (indicated as "H:HC") in the streams are summarized in Table 1.

TABLE 1

| | Reactors with interstage heat exchanger cooling | | | | | | | |
|---|---|---|---|---|---|---|---|---|
| | Reactor | | | | | | | |
| | 100 | | 200 | | 300 | | 400 | |
| Stream | 31 | 30 | 41 | 40 | 51 | 50 | 61 | 60 |
| Temperature (° C.) | 430 | 470 | 430 | 470 | 430 | 470 | 430 | 470 |
| Flowrate (kg/h) | 10000 | 10000 | 10000 | 10000 | 10000 | 10000 | 10000 | 10000 |
| H:HC | 3.0 | 2.1 | 2.1 | 1.6 | 1.6 | 1.1 | 1.1 | 0.9 |

In this example, the heat exchangers are required for cooling the effluent from the previous catalyst bed.

Example 2 (Comparative): Series of Reactors with Pure H2 Coldshot Cooling

The hydrocarbon feed is subjected to hydrocracking by a system as illustrated in FIG. 2. H2 is introduced at each stage of the reactor to control the temperature. The temperature and the molar ratio of hydrogen to hydrocarbon (indicated as "H:HC") in the streams are summarized in Table 2.

TABLE 2

| | Reactors with pure H2 coldshot cooling | | | | | | | |
|---|---|---|---|---|---|---|---|---|
| | Reactor | | | | | | | |
| | 100 | | 200 | | 300 | | 400 | |
| Stream | 31 | 30 | 41 | 40 | 51 | 50 | 61 | 60 |
| Temperature (° C.) | 430 | 473 | 430 | 475 | 435 | 473 | 434 | 470 |
| Flowrate (kg/h) | 10000 | 10000 | 10500 | 10500 | 11000 | 11000 | 11550 | 11550 |
| H:HC | 3.0 | 2.1 | 3.0 | 2.2 | 2.9 | 2.4 | 3.0 | 2.7 |

In this example, the heat exchangers are not required for cooling the effluent from the previous catalyst bed. Instead, the effluent from the previous catalyst bed is mixed with a stream of H2 of room temperature (cold shot) in quench zones between catalyst beds. The cold shot decreases the effluent temperature while increasing the ratio between hydrogen and hydrocarbons.

Use of only hydrogen results in a high H2:hydrogen ratio in each of the reaction zones. The large amount of hydrogen leads to a large reactor size which is undesirable.

Example 3 (Comparative): Series of Reactors with Pure Naphtha Coldshot Cooling

The hydrocarbon feed is subjected to hydrocracking by a system as illustrated in FIG. 3. Hydrocarbon is introduced at each stage of the reactor to control the temperature. The temperature and the molar ratio of hydrogen to hydrocarbon (indicated as "H:HC") in the streams are summarized in Table 3.

TABLE 3

| | Reactors with pure naphtha coldshot cooling | | | | | | | |
|---|---|---|---|---|---|---|---|---|
| | Reactor | | | | | | | |
| | 100 | | 200 | | 300 | | 400 | |
| Stream | 31 | 30 | 41 | 40 | 51 | 50 | 61 | 60 |
| Temperature (° C.) | 430 | 473 | 436 | 472 | 433 | 475 | 442 | 487 |
| Flowrate (kg/h) | 7500 | 7500 | 8300 | 8300 | 9200 | 9200 | 10000 | 10000 |
| H:HC | 3.0 | 2.1 | 1.9 | 1.4 | 1.3 | 0.9 | 0.9 | 0.6 |

In this example, the heat exchangers are not required for cooling the effluent from the previous catalyst bed. Instead, the effluent from the previous catalyst bed is mixed with a stream of hydrocarbon of room temperature (cold shot) in quench zones between catalyst beds. The cold shot decreases the effluent temperature while decreasing the ratio between hydrogen and hydrocarbons.

Use of only hydrocarbon eventually results in a H2:hydrocarbon ratio which is too low. Although a low H2:hydrocarbon ratio is advantageous for achieving a small reactor size, the H2:hydrocarbon ratio is too low in the last reaction zone to avoid a high risk of catalyst deactivation in the last reaction zone in this example.

Example 4: Series of Reactors with HC—H2 Mixture Coldshot Cooling

The hydrocarbon feed is subjected to hydrocracking by a system as illustrated in FIG. 4. A mixture of hydrogen and hydrocarbon is introduced at each stage of the reactor to control the temperature. The temperature and the molar ratio of hydrogen to hydrocarbon (indicated as "H:HC") in the streams are summarized in Table 4.

TABLE 4

Reactors with hydrogen_naphtha mixture coldshot cooling

| | Reactor | | | | | | | |
|---|---|---|---|---|---|---|---|---|
| | 100 | | 200 | | 300 | | 400 | |
| Stream | 31 | 30 | 41 | 40 | 51 | 50 | 61 | 60 |
| Temperature (° C.) | 430 | 474 | 433 | 480 | 435 | 485 | 435 | 488 |
| Flowrate (kg/h) | 6000 | 6000 | 7000 | 7000 | 8300 | 8300 | 10000 | 10000 |
| H:HC | 3.0 | 2.1 | 2.2 | 1.5 | 1.6 | 1.1 | 1.3 | 0.9 |

In this example, the heat exchangers are not required for cooling the effluent from the previous catalyst bed. Instead, the effluent from the previous catalyst bed is mixed with a mixture of H2 and hydrocarbon of room temperature (cold shot) in quench zones between catalyst beds. The cold shot decreases the effluent temperature while slightly increasing the ratio between hydrogen and hydrocarbons.

Example 5: Series of Reactors with Alternate HC and Hydrogen Coldshot Cooling The hydrocarbon feed is subjected to hydrocracking by a system as illustrated in FIG. 5. A stream of hydrogen or a stream of hydrocarbon is introduced at each stage of the reactor to control the temperature. The temperature and the molar ratio of hydrogen to hydrocarbon (indicated as "H:HC") in the streams are summarized in Table 5.

TABLE 5

Reactors with hydrogen and naphtha coldshot cooling

| | Reactor | | | | | | | |
|---|---|---|---|---|---|---|---|---|
| | 100 | | 200 | | 300 | | 400 | |
| Stream | 31 | 30 | 41 | 40 | 51 | 50 | 61 | 60 |
| Temperature (° C.) | 430 | 474 | 433 | 470 | 431 | 474 | 435 | 472 |
| Flowrate (kg/h) | 7800 | 7800 | 8700 | 8700 | 8950 | 8950 | 10000 | 10000 |
| H:HC | 3.0 | 2.1 | 1.9 | 1.4 | 2.3 | 1.7 | 1.6 | 1.3 |

In this example, the heat exchangers are not required for cooling the effluent from the previous catalyst bed. Instead, the effluent from the previous catalyst bed is mixed with a stream of H2 or hydrocarbon of room temperature (cold shot) in quench zones between catalyst beds. The cold shot decreases the effluent temperature while changing the ratio between hydrogen and hydrocarbons.

A hydrocarbon stream is fed as cold shot to the effluent from the first bed. This leads to a decrease in H:HC ratio. A hydrogen stream is fed as cold shot to the effluent from the second bed, leading to an increase in the H:HC ratio. Subsequently, a hydrocarbon stream is fed as cold shot to the effluent from the third bed. This leads to a decrease in H:HC ratio.

By injecting the hydrocarbon stream and the hydrogen stream alternately, the ratio between hydrogen and hydrocarbons is adjusted to be relatively stable. The H2:hydrocarbon ratio can be controlled such that it is sufficiently low for achieving a small reactor size while being maintained within the desired range.

The invention claimed is:

1. A process for hydrocracking a feedstream comprising hydrocarbons to obtain BTX in a gas phase hydrocracking reactor system which comprises
   (i) an upstream end and a downstream end,
   (ii) a plurality of successive reaction zones distributed along the reactor system between the upstream end and the downstream end, wherein each of the reaction zones has a bed of a hydrocracking catalyst contained therein and
   (iii) a plurality of quench zones, the quench zones being distributed along the reactor system and each being situated between successive reaction zones,
   wherein the process comprises:
   (a) injecting a first portion of a hydrogen gas into the upstream end and a first portion of a hydrocarbon gas into the upstream end and (b) injecting a second portion of the hydrogen gas into at least one of the quench zones and injecting a second portion of the hydrocarbon gas into at least one of the quench zones, wherein a molar ratio between hydrogen and hydrocarbons entering each of the reaction zones is 1:1 to 4:1, wherein the molar ratio between hydrogen and hydrocarbons entering the reaction zones decreases with the distance of the reaction zone from the upstream end of the reactor system; and wherein the hydrocracking the feedstock produces the BTX in the reaction zones.

2. The process according to claim 1, wherein either the hydrocarbon gas or the hydrogen gas is injected into each of the quench zones.

3. The process according to claim 2, wherein the hydrocarbon gas and the hydrogen gas are injected into the quench zones in an alternating fashion such that either the hydrocarbon gas or the hydrogen gas is injected in one quench zone and the other gas is injected in a subsequent quench zone.

4. The process according to claim 1, wherein a mixture of the hydrocarbon gas and the hydrogen gas is injected into each of the quench zones.

5. The process according to claim 1, wherein the gas phase hydrocracking reactor system comprises a single reactor comprising the reaction zones and the quench zones.

6. The process according to claim 1, wherein the molar ratio between hydrogen and hydrocarbons entering the reaction zone closest to the downstream end is at least 25% lower than the molar ratio between hydrogen and hydrocarbons entering the reaction zone closest to the upstream end.

7. The process according to claim 1, wherein the molar ratio between hydrogen and hydrocarbons entering the reaction zone closest to the upstream end is 1.5:1 to 4:1 and/or the molar ratio between hydrogen and hydrocarbons entering the reaction zone closest to the downstream end is 1:1 to 3:1.

8. The process according to claim 1, wherein a hydrocracking product stream from the downstream end of the reactor system has a molar ratio between hydrogen and hydrocarbon of at most 2:1.

9. The process according to claim 1, wherein the hydrocarbon gas comprises C5-C12 hydrocarbons.

10. The process according to claim 1, wherein the hydrocarbon gas comprises first stage or multi-stage hydro-treated pyrolysis gasoline, straight run naphtha, hydrocracked gasoline, light coker naphtha and coke oven light oil, FCC gasoline, reformate, FT (Fischer-Tropsch) or synthetic naphtha or mixtures thereof.

11. The process according to claim 1, wherein the hydrocracking catalyst comprises 0.01-1 wt-% hydrogenation metal in relation to the total catalyst weight and a zeolite having a pore size of 5-8 Å and a silica ($SiO_2$) to alumina ($Al_2O_3$) molar ratio of 5-200 and wherein process conditions in each of the reaction zones include a temperature of 425-580° C., a pressure of 300-5000 kPa gauge and a Weight Hourly Space Velocity of 0.1-15 $h^{-1}$.

12. The process according to claim 11, wherein the zeolite is a ZSM-5 zeolite.

13. The process according to claim 11, wherein the hydrogenation metal is platinum.

14. The process according to claim 11, wherein the hydrocracking catalyst comprises the hydrogenation metal deposited on the zeolite.

\* \* \* \* \*